United States Patent
Fuhr et al.

(10) Patent No.: US 7,892,815 B2
(45) Date of Patent: Feb. 22, 2011

(54) DEVICE AND METHOD FOR CONDITIONING BIOLOGICAL CELLS

(75) Inventors: Guenter Fuhr, Berlin (DE); Heiko Zimmermann, St. Ingbert (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 12/678,544

(22) PCT Filed: Sep. 17, 2008

(86) PCT No.: PCT/EP2008/007780

§ 371 (c)(1),
(2), (4) Date: Mar. 17, 2010

(87) PCT Pub. No.: WO2009/043484

PCT Pub. Date: Apr. 9, 2009

(65) Prior Publication Data

US 2010/0196946 A1 Aug. 5, 2010

(30) Foreign Application Priority Data

Sep. 28, 2007 (DE) .................. 10 2007 046 516

(51) Int. Cl.
*C12M 1/34* (2006.01)
*C12M 3/00* (2006.01)
(52) U.S. Cl. ................... 435/287.1; 435/29; 435/289.1; 435/297.1; 435/297.2; 435/309.1
(58) Field of Classification Search .................. 422/63; 435/29, 289.1, 297.1–297.2, 287.1, 305.1, 435/309.1
See application file for complete search history.

(56) References Cited

U.S. PATENT DOCUMENTS 4,894,343 A * 1/1990 Tanaka et al. ............ 435/285.2

(Continued)

FOREIGN PATENT DOCUMENTS

WO WO9828405 * 7/1998

(Continued)

OTHER PUBLICATIONS

Gerhart, "1998 Warkany Lecture: Signaling Pathways in Development", Teratology, vol. 60, pp. 226-239 (1999).

(Continued)

*Primary Examiner*—Walter D Griffin
*Assistant Examiner*—Shanta G Doe
(74) *Attorney, Agent, or Firm*—Caesar, Rivise, Bernstein, Cohen & Pokotilow, Ltd.

(57) ABSTRACT

A conditioning device (100) for biological cells includes a support (10), adapted to support at least one biological cell (1) in a supporting zone (11), and a contact device (20), adapted to support at least one conditioning sample (3) and to displace the at least one conditioning sample (3) relative to the support (10) in such a manner that the at least one conditioning sample (3) touches the at least one biological cell (1), the contact device (20) including at least two mechanical supporting elements (21, 22) that can be displaced from various spatial directions towards the support (10). The invention also relates to methods for conditioning, especially imprinting or differentiating biological cells and to uses of the conditioning device.

25 Claims, 4 Drawing Sheets

U.S. PATENT DOCUMENTS

| | | | |
|---|---|---|---|
| 5,882,929 A * | 3/1999 | Fofonoff et al. | 435/395 |
| 6,060,306 A * | 5/2000 | Flatt et al. | 435/297.2 |
| 6,541,243 B1 | 4/2003 | Harris et al. | |
| 6,991,906 B1 | 1/2006 | Fuhr et al. | |
| 2005/0158845 A1 | 7/2005 | Wikswo et al. | |
| 2007/0212773 A1* | 9/2007 | Fujii et al. | 435/287.1 |
| 2008/0038806 A1* | 2/2008 | Fuhr | 435/173.1 |

FOREIGN PATENT DOCUMENTS

| | | | |
|---|---|---|---|
| WO | WO2004074426 | * | 9/2004 |
| WO | 2005083057 A1 | | 9/2005 |
| WO | 2006059109 A1 | | 6/2006 |

OTHER PUBLICATIONS

International Search Report for PCT/EP2008/007780.

* cited by examiner

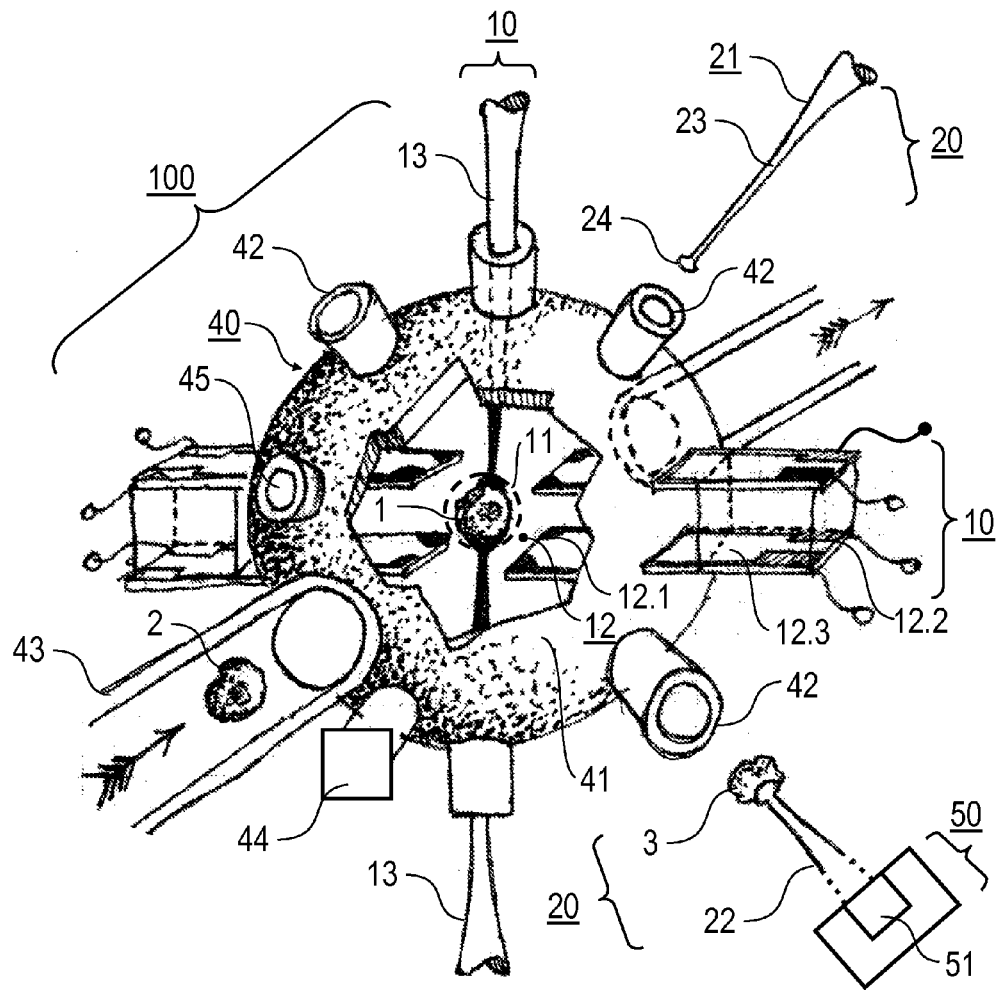
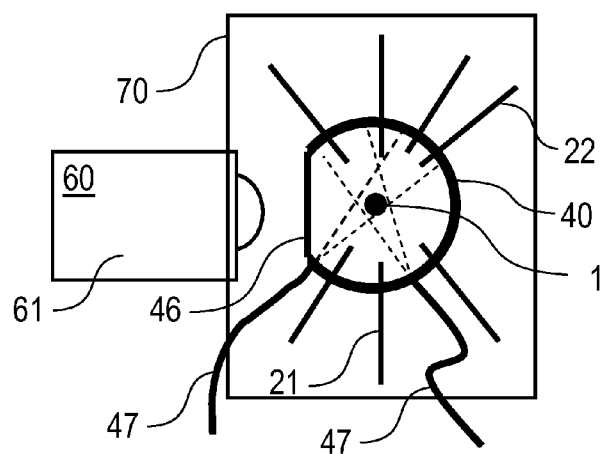

DEVICE AND METHOD FOR CONDITIONING BIOLOGICAL CELLS

BACKGROUND OF THE INVENTION

The invention relates to a conditioning device for biological cells, in particular a conditioning device for conditioning, e.g., manipulation, stimulation, imprinting and/or differentiation of biological cells by an interaction with a conditioning sample. Main applications of the conditioning device consist in the conditioning of biological cells and the examination of their reactions after a contacting by the conditioning sample. Furthermore, the invention relates to conditioning methods that can be realized in particular with the conditioning device.

Biological cells, in particular animal or human cells, are permanently in interaction with adjacent cells, biological surfaces or liquids in the organism. Intermolecular interactions take place between surface molecules of adjacent cells or between surface molecules of a cell with adjacent substances. Molecular surface bondings can be exchanged and molecular signal chains can be induced in the participating cells. The signal chains propagate, e.g., into the cytoplasm, where they influence cell development procedures such as, e.g., the expression of genes (see J. Gerhart in "Theratology", vol. 60, 1999, pp. 226-239).

For example, a cell differentiation can be initiated or influenced by surface interactions of biological cells. Furthermore, the surface interaction can effect the formation of tissue from biological cells. In pronounced form processes of the signal exchange and of a so-called cellular synchronization can be observed in particular in the cell differentiation or wound healing. Especially the differentiation and multiplication of stem cells is based on the bonding of surface receptors of the stem cells to ligands. During the embryogenesis or a regeneration of tissue (e.g. wound healing) changes of biological cells are induced by surface contacts.

Biologically active molecules, i.e., molecules that induce a change of the biological cell upon contact with the biological cell, in particular the cell surface, are also designated as signal factors. A distinction is made between soluble signal factors that are contained, e.g., in a cultivation medium or a body fluid and surface-bound signal factors that are arranged, e.g., on cell surfaces or on surfaces of aggregates of biological substances or boundary surfaces in the biological organism.

The in vitro examination of the change of biological cells after a contact with the signal factor represents an extremely complex problem for the following reasons. In the first place, every contact of a cell with a molecule in the environment can induce a biologically active interaction. Every contact can represent a piece of molecular information for the cells so that signal chains with changes of cellular states can be initiated. For an examination of the physiologically relevant signal factors false molecular information such as can occur, e.g., by a contact with an artificial surface such as glass, metal or plastic must be avoided by the creation of defined environmental conditions of the cell. However, such artificial surfaces are permanently present in the conventional techniques of cellular biology, e.g., as parts of culture vessels or instruments. In the second place, the in vitro examination becomes complex since a large number of signal factors and signal chains are known that act specifically on cells. In order to test the effect of a certain signal factor or of combinations of signal factors extremely many parameter variations are necessary, e.g., in order to identify one of the 17 signal paths known today of the higher animal cells for which some 10 to some 100 signal factors are active (see above publication of J. Gerhart).

A known concept for the conditioning and in-vitro examinations of biological cells is based on arranging the cells during a test exclusively in a physiological solution or on a surface that is recognized by the cell as physiological surface or at least not as artificial surface. In doing so, a contactless manipulation of the cells takes place, e.g., by dielectrophoretic or optical forces in order to avoid undesired surface contacts.

A generic conditioning method for carrying out this concept is known, e.g., from U.S. Pat. No. 6,991,906 B1. In this technique, which is schematically illustrated in FIG. 9, a first cell 1 is held with a holding device 10' comprising a group of electrodes for forming a dielectrophoretic field cage 12'. An optical tweezer 20' is used to hold a second cell 2 and for its movement toward the first cell 1. The second cell 2 forms a sample for the stimulation of the first cell 1. The second cell 2 can be brought in contact with the first cell 1 by the movement of the focus of the optical tweezer 20'. After an interaction an examination of the first cell 1 or a separation of the cells 1, 2 can take place using the optical tweezer 20'.

The technique according to FIG. 9 has a number of disadvantages that limit a practical application for in-vitro examinations. A first disadvantage results from the fact that only individual cell-cell interactions can be examined. For an approach of two cells (or other samples) to the cell 1 two optical tweezers would be required that would, however, mutually disturb one another. Furthermore, the cell 2 can only be moved from certain directions, in particular from above to cell 1, since otherwise the optical tweezer 20' is shaded by the electrodes 13' or the cell 1. It can also be disadvantageous that a high light intensity in the focus of the optical tweezer 20' has an undesired influence on the cells or their interactions. Finally, the low trapping forces of the optical tweezer 20' are a disadvantage. Two cells 1, 2 can no longer be separated from one another without problems with the optical tweezer 20' after the mutual contacting and formation of intermolecular interactions.

A further generic technique for carrying out the above-named concept is described in WO 2005/083057. In this technique the cell to be examined is arranged on a magnetic carrier that can be shifted under the action of a magnetic field on the bottom of a conduit filled with liquid. A further cell that is to be made to interact with the first cell can be arranged on a further magnetic carrier that is shiftably arranged especially on a cover element of the conduit opposite the bottom. The cells can be made to interact with one another by a suitable alignment of the magnetic carriers. Even the technique described in WO 2005/083057 has the disadvantage that only individual cell-cell interactions can be examined. The geometric extension of the magnetic carriers prevents several cells from being brought in contact independently of each other with a cell to be examined. A further disadvantage consists in that only one-sided cell contacts are possible. The cell surface available for the examination is greatly limited by the depositing on the magnetic carrier. Finally, a disadvantage consists in that only global cell-cell interactions can be examined. The cell contact can not be limited to certain parts of the cell surface when using the magnetic carriers.

Thus, the previous techniques for carrying out the above-mentioned concept for in-vitro examinations are limited to special applications (e.g. examinations on planar surfaces, one-sided cell treatment). A tool for the handling of biological cells that is related to solutions and surfaces and that makes possible precise and reliable tests even for complex combinations of signal factors has, however, not been available yet.

The invention has the objective of providing an improved conditioning device for handling biological cells, in particular for purposes of testing, manipulation or examination, with which the disadvantages and limitations of the conventional techniques are avoided. The objective of the invention is furthermore to provide an improved conditioning method that is suitable for an in-vitro conditioning of biological cells.

These objectives are solved by a conditioning device and a conditioning method of the invention.

SUMMARY OF THE INVENTION

According to a first aspect the invention is based on the general technical teaching of further developing a generic conditioning device with a holding device for holding at least one biological cell and with a contact device for holding and moving at least one conditioning sample so that it contacts at least one biological cell in such a manner that the contact device comprises at least two mechanical carrier elements that can move relative to the holding device. The carrier elements carry the at least one conditioning sample on their free ends that face the holding area. The carrier elements can preferably move from different spatial directions, in particular under different spatial angles from several sides toward the holding device and away from it.

Providing the at least two carrier elements considerably broadens the functionality of the conditioning device in comparison to the conventional techniques. Thus, the carrier elements of the contact device can fulfill different functions depending on the concrete test task. One or more carrier elements can carry one or different conditioning samples and be pushed with them to a holding area of the holding device while a further carrier element is arranged adjacent to the holding area in order to form a mechanical stop for the at least one cell in the holding area during the contacting by the other carrier elements. According to another variant all carrier elements can carry one or different conditioning samples that are put in contact with the at least one cell in the holding area.

The term "conditioning" designates here the provision of a pre-determined molecular interaction of a cell with a sample (conditioning sample). The conditioning can also be designated in general as stimulation, imprinting or differentiation. A targeted imitation of a real procedure (molecular interaction of the cell with the environment) takes place with the conditioning in a model environment that is formed in the conditioning device.

A further important advantage of the invention results from the fact that the carrier elements constitute mechanical components formed from a solid material. The at least one conditioning sample is, deviating from the conventional technique (e.g., according to FIG. 9), not contactless but rather moves with mechanically transferred drive forces. This can advantageously improve the precision of the positioning of the conditioning sample upon the contacting of the cell in the holding area. Furthermore, a mutual interaction of the carrier elements such as would occur, e.g., with optical tweezers, is excluded. Finally, increased forces during the contact of the conditioning sample with the cell or during its separation are exerted with the carrier elements used according to the invention in comparison to the conventional technique.

A further important advantage of the conditioning device is that the carrier elements are movable along different spatial directions. The movement along different spatial directions means that the directions of movement of two of the at least two mechanical carrier elements set a plane that also contains the holding area of the holding device. A multi-sided arrangement of the carrier elements on the cell is advantageously provided in the holding area, wherein free ends of the carrier elements (so-called stamping surfaces) face towards the holding area. The multi-sided arrangement (arrangement on several sides of the cell) advantageously excludes a mutual disturbance of the movement of the carrier elements and/or a mutual influencing of optionally different conditioning samples on the carrier elements. The longitudinally extended, preferably straight form of the carrier elements, which can have a tapering (e.g. conical form) in particular on their free ends facing the holding area, has the additional advantage that the positioning of the carrier elements is limited to certain desired spatial areas.

A further important advantage of the invention consists in that parallel or successively following complex surface contacts can be realized on cells in freely selectable combination. The surface contacts can be formed in such a manner that they act only on a partial area of the surface of the cell, which partial area can be selected as a function of the concrete application of the invention. Furthermore, it can be ensured that no undesired, non-specific surface contacts take place on the cell to be examined in addition to the intended surface contacts.

According to a second aspect the invention is based on providing a conditioning method for the conditioning of at least one biological cell with at least one conditioning sample, in particular for a subsequent examination of the cell, in which method the conditioning device according to the invention is preferably used. The conditioning method comprises the steps of the providing the at least one cell in the holding area of the holding device and the at least one conditioning sample on at least one of the carrier elements as well as the movement of at least one of the at least two carrier elements in such a manner that the cell is contacted by at least one conditioning sample. The cell can be advantageously subjected to a contact by the at least one conditioning sample that is determined in time and/or locally. The conditioning preferably takes place free of destruction, i.e., signals, e.g., for the cell differentiation can be exerted on the cell with the at least one conditioning sample without destroying the cell, in particular without penetrating the cell membrane.

A further advantage of the invention consists in the variability in the design of the holding device. Thus, the holding device can be adapted according to a first variant to hold the at least one biological cell with forces acting in a contactless manner, e.g., under the action of dielectric forces or optical forces. In this instance, in which the holding can take place without contacting solid surfaces, the holding device comprises, e.g., a dielectric field cage such as is known from the fluidic microsystem technology, or an optical tweezer. The holding area is formed correspondingly by a field minimum in the field cage or the focus of the optical tweezer. This variant of the invention has the advantage that the cell can be moved gently with known methods into the holding device and positioned there. The problem of reduced holding forces occurring, for example, in the conventional technology according to FIG. 9, is avoided since the carrier elements are used for exerting forces of holding, contacting and/or separation in the interaction of the cell with the conditioning sample.

A method can advantageously be realized with the contactless holding of the at least one biological cell in which the cell is at first trapped with relatively weak forces and held. The conditioning subsequently takes place using the mechanical carrier elements, which can be separated afterwards from the cell using relatively strong forces.

According to a second variant of the invention the holding device can have at least one holding surface on which the at least one biological cell can be positioned. In this instance the holding does not take place in a contactless manner but rather in contact with the holding surface. The holding surface can be, e.g., part of at least one mechanical holding element that is constructed like the carrier elements and is movable. Furthermore, the holding surface can generally be a fixed surface or a boundary surface between two liquids with different viscosities, e.g., between two cultivation phases. The positioning of the cell on the holding surface can be advantageous with regard to an elevated stability of the stationary holding in the holding device.

The holding surface advantageously carries a biocompatible coating that is biochemically inactive for the cell in the holding device. The biocompatible coating is biochemically inactive if no change of the cell or a predetermined change that is not critical in the current test task is induced upon deposition of a cell on the holding surface and an optionally occurring intermolecular interaction of the cell with the biocompatible coating. Examples for biocompatible coatings that can be used for various test tasks and various cell types comprise fibronectin, collagen or immobilized molecules of signal factors for the differentiation of cells such as, e.g., IGF 1 (insulin-like growth factor), BMP2 (bone morphogenetic protein 2), BMP7 (bone morphogenetic protein 7), VEGF (vascular endothelial growth factor) or TGFB3 (transforming growth factor).

The holding device can also embody both cited variants, thus, it can be adapted to hold the cell with forces acting in a contactless manner as well as with a mechanical contact with the holding surface. It can be provided, e.g., that in a first phase (providing of the cell in the holding area) a contactless holding takes place and in a second phase (contacting of the cell in the holding area with the conditioning sample) a contact holding with the holding surface takes place.

According to a preferred embodiment of the invention the holding device is arranged in a container adapted to receive a liquid cultivation medium. Predetermined cultivation conditions can advantageously be set in the container with the cultivation medium. The cultivation medium can be used to nourish the at least one cell in the holding device and/or as additional test substance. The cultivation medium can, e.g., contain one (or several) differentiation factor(s) whose effect is examined in conjunction with the effect of the at least one conditioning sample on the carrier elements.

According to an advantageous design of the conditioning device according to the invention the container has an inner volume that is at least equal to four times the volume of the at least one biological cell in the holding area. This condition is typically fulfilled when the inner volume is at least equal to four times the volume of the holding area (e.g., the volume of the effective field minimum in the field cage). The inner volume is especially preferably greater than the 10-fold to 100-fold volume of the at least one biological cell or of the holding area, respectively. This can advantageously create a sufficiently large cultivation space for the at least one biological cell and also space for investigations of the cell, e.g., optical observations or impedance measurements. The inner volume of the container is selected to be especially preferably in the range of $4 \times 10^3$ $\mu m^3$ to 1000 $mm^3$.

The container of the conditioning device according to the invention can advantageously assume further functions with which the applicability of the invention is significantly extended. Thus, at least one support can be provided in a wall of the container that is adapted to guide the movement of at least one of the mechanical carrier elements. One support for one of the at least two carrier elements can be sufficient for carrying out the invention, in which case the other carrier element is moved or arranged without a support. However, an embodiment of the invention is preferred in which several supports are provided in the container wall whose number is equal to the number of the mechanical carrier elements. In this case the directions of movement of the carrier elements can be advantageously determined by the supports in the container wall. Furthermore, at least one fluid conduit can be provided that runs through the container wall and establishes a fluid connection between the inner space of the container and an environment of the container, e.g., a connected fluidic system. The fluid conduit can advantageously be used to transport the at least one biological cell into the holding device. Furthermore, the at least one fluid conduit can be used for a supply and/or an exchange of the cultivation liquid in the container. Furthermore, the container can fulfill a measuring function if it is equipped with at least one sensor for the detecting of a physical or chemical quantity in the container. The sensor can comprise, e.g., a photosensor and/or an impedance sensor. For purposes of illumination and examination it can furthermore be advantageous if the container contains at least one optical element provided in the container wall in order to couple light into the interior of the container, in particular into the holding area of the holding device and/or to detect light from the holding area. The optical element can comprise, e.g., an optical window in the container wall, imaging optics and/or optical waveguides.

According to a further preferred embodiment of the invention it is provided that at least one of the carrier elements, but preferably all carrier elements have a straight rod form. The carrier elements comprise a carrier rod that can be shifted in the supports in the container wall. The carrier element has a stamping surface that is used as receptacle for the conditioning sample and is on the free end of the carrier rod facing the holding area of the holding device, i.e., facing the biological cell.

The stamping surface is preferably smaller than the surface of the at least one biological cell, in particular smaller than the surface of the holding area. A preferred cross-sectional surface of the stamping surface is selected in the range of 1 $\mu m^2$ to 10,000 $\mu m^2$. This advantageously makes possible the simultaneous contacting of the surface of the at least one biological cell with a plurality of carrier elements and/or the contacting of certain surface areas, e.g., in the vicinity of certain membrane organelles of the cell as a function of the concrete examination task.

The stamping surface preferably has a concave, convex or plane form. The concave form has the advantage that upon the contacting of the stamping surface with the cell to be examined its membrane is stretched, so that an improved surface contact is formed. The convex form can have advantages for a protection of the conditioning sample on the stamping surface during the movement of the carrier element. Advantages of a plane form of the stamping surface can result in particular for certain additional functions of the conditioning device, e.g., during the formation of a cell group in the holding device. Alternatively or additionally, the stamping surface can have a microstructuring such as, e.g., projections with typical dimensions in the range of 50 nm to 5 $\mu m$. According to a further alternative a test coating can be provided on the stamping surface which coating forms the conditioning sample of the particular carrier element. The test coating comprises biologically active molecules such as, e.g., the above-mentioned signal factors. Combinations of the mentioned forms, structures and test coatings can be provided as a function of the concrete test task.

The carrier elements of the conditioning device can be moved manually if required. However, according to a further advantageous embodiment the conditioning device is equipped with a drive device with which at least one of the carrier elements can be moved. The drive device is positioned stationarily relative to the container of the conditioning device so that a precise and reproducible movement of the carrier elements can be advantageously realized. The drive device particularly preferably comprises at least one piezoelectric drive. Typically, a plurality of piezoelectric drives is provided whose number corresponds to the number of the carrier elements and optionally of the holding elements. Each carrier element or holding element is provided with an independent piezoelectric drive so that there is advantageously a great flexibility in the selective actuation of individual carrier elements.

The drive device is particularly preferably formed in such a manner that the carrier elements can be shifted on straight movement tracks that are radially aligned relative to the holding area. This makes possible a contacting on all sides of the at least one biological cell in the holding area. The movement of the carrier elements on straight tracks to the holding area is supported by a form of the carrier elements that tapers conically to their free ends.

The carrying out of the invention is not limited to providing two carrier elements. Depending on the concrete test task, more than two carrier elements, in particular at least 10 carrier elements, especially preferably at least 20 carrier elements, e.g., up to 50 or 100 or even more than 100 carrier elements can be provided. A high combinatorial plurality in the adjustment of different test conditions can be achieved by the selective control of the individual carrier elements.

In order to realize the conditioning method according to the invention it can be sufficient to contact the cell to be examined with one or several conditioning samples. After the conditioning the cell can be removed from the conditioning device and at first stored and/or subjected to a cultivation. However, according to a preferred embodiment of the invention it is provided that after a contacting phase in which one or several conditioning samples were brought in contact with the cell at the same time or staggered in time an examination of the cell is provided. The examination can advantageously take place in the conditioning device, e.g., by optical or electrical measurements according to known measuring methods which are known as such. Alternatively, the cell can be transferred for the examination out of the conditioning device into a separate measuring instrument.

According to a further variant the conditioned cell can be subjected to a further cultivation (especially long-time culture) after the induction of a differentiation in order to form cell groups of differentiated cells. These cell groups can advantageously be used in methods of "tissue engineering".

A further advantage of the invention consists in the high variability in the selection of the conditioning sample, that preferably comprises signal molecules (e.g. BMP2, BMP7, IGF), biologically active macromolecules (e.g. vitamins, hormones), biological cells (e.g. differentiated cells or precursor cells), cell components (e.g. cell components of differentiated cells, especially membrane components) and/or microstructured surfaces as a function of the test task.

If, according to a further variant of the invention, the at least one carrier element is moved at a speed selected in the range of 5 μm/h to 10 mm/h, this can result in advantages for a physiologically gentle contacting of the at least one biological cell. At speeds in the cited interval the cells can adapt to the approaching carrier element on account of their natural reorganization of the molecular cell contacts of the cell membrane. This advantageously achieves an especially effective cell contact.

The conditioning method according to the invention can advantageously be combined with further examination and/or manipulation steps. The further steps comprise, e.g., a provision of a conditioning sample as component of a cultivation liquid that surrounds the at least one biological cell, a formation of a hollow space surrounding the at least one biological cell, which space is enclosed by stamping surfaces of carrier elements and/or holding surfaces of holding elements, a measuring of interaction forces between the cell and the conditioning sample, in which molecular bonding forces of the cell membrane of the examined cell can be detected, a mechanical deformation of the at least one biological cell, in which elastic properties of the cell plasma are detected and conclusions about the physiological state of the cell are made possible, a liquid treatment of the at least one biological cell in the holding area of the holding device, an encapsulation of the at least one biological cell, and/or a transfer of the cell into a frozen state.

BRIEF DESCRIPTION OF SEVERAL VIEWS OF THE DRAWINGS

Further details and advantages of the invention are described in the following with reference made to the attached drawings, in which:

FIG. 1 shows a first embodiment of the conditioning device according to the invention in schematic perspective view;

FIG. 2 shows an illustration of an embodiment of the method according to the invention in which an optical examination is provided;

DETAILED DESCRIPTION OF PREFERRED EMBODIMENTS

Figure 3:
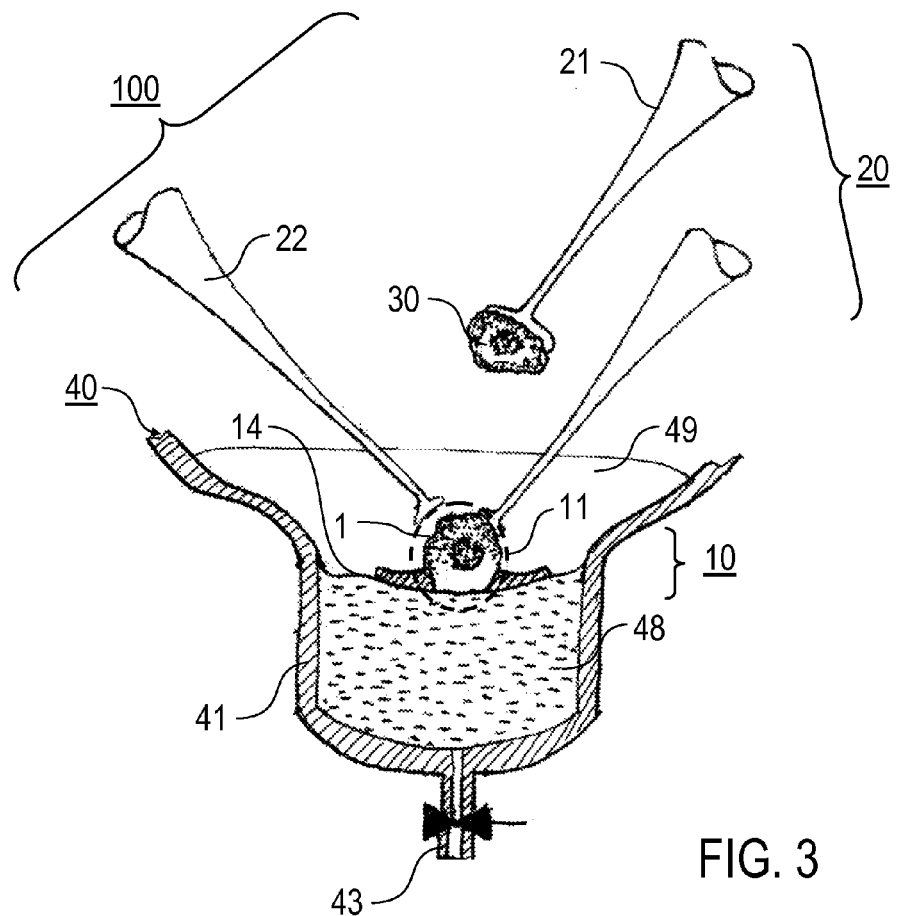
FIG. 3 shows a further embodiment of the conditioning device according to the invention.

The invention is described in the following in particular with reference made to details of the holding of the cell to be examined and of the properties and handling of the conditioning device, in particular of the carrier elements. Details of the cultivation of cells or manipulation of cells under the effect of high-frequency electrical fields by means of negative dielectrophoresis are not described here since they are known from the state of the art. The invention is explained by way of example with reference made to the test with a single cell. The carrying out of the invention is, however, not limited to this variant. By way of replacement, several cells can be arranged in the holding device and subjected as cell aggregate to a test like a single cell.

FIG. 1 shows a first embodiment of a conditioning device 100 according to the invention with a holding device 10 and a contacting device 20 that are attached in or at a container 40 with a container wall 41. The holding device 10 has a holding area 11 formed by the field minimum of a dielectrical field cage 12 and/or holding elements 13.

The dielectrical field cage 12 comprises eight electrodes 12.1 that are connected via electrode connections 12.2 to a voltage source (not shown). The electrodes 12.1 and the electrode connections 12.2 are arranged on electrode carriers 12.3. The electrode carriers 12.3 comprise rectangular plates shiftably arranged in slot-shaped openings of the container 40. When the electrodes 12.1 are loaded with high-frequency electrical voltages the desired field minimum is formed in the dielectrical field cage 12 in which a cell 1 is arranged under the action of dielectrophoretic forces.

The holding elements 13 of the holding device 10 are additionally provided for the mechanical holding of cell 1. The holding elements 13 comprise movable rod elements constructed like the carrier elements of the contact device 20 (see below).

The contact device 20 comprises a plurality of carrier elements of which only two carrier elements 21, 22 are shown by way of example in FIG. 1. Each carrier element 21, 22, that comprises a carrier rod 23 and a stamping surface 24 (see FIG. 5 for details), is shiftably arranged in a support 42 in the container wall 41. The carrier rod 23 can have a conical form tapering to the stamping surface 24, as shown. Alternatively, the carrier rod 23 can have a straight, e.g., cylindrical rod form. In order to move the carrier elements 21, 22 a drive device 50 (schematically shown at carrier element 22) is provided that comprises a piezoelectric drive 51 or a servomotor on each carrier element 21, 22. The carrier elements 21, 22 are moved according to the invention in the direction of their longitudinal extension (rod form).

In order to prevent a migration of cells along the carrier elements on account of a natural cell movement the carrier rods 25 are preferably provided with a coating that prevents or suppresses a cell adhesion. The coating comprises, e.g., a water repellent, a PTFE coating or a surface layer modified by a plasma treatment.

The container wall 41, that is shown partially perforated in FIG. 1 for purposes of illustration, can form, e.g., a spherical form. The diameter of the container 40 can be selected in the range of, e.g., 100 µm to a few centimeters as a function of the concrete usage of the invention. The fewer cells that are to be tested the smaller the sphere volume selected in order that the formation of physiological conditions in the interior of the container 40 is facilitated and in particular it is made possible that the cell conditions the liquid in its environment. The container wall 41 can be transparent in order to make possible an all-sided observation of the cell 1 in the holding device 10.

The supports 42 have typical diameters in the range of 50 µm to a few mm. A seal of the supports 42 is not necessary given suitable dimensioning, so that liquids in the support 42 are held by capillary forces. Alternatively, a seal, e.g., of an elastic material can be provided. The supports 42 can be formed by the container wall 41 in that it is produced with a sufficient thickness, e.g., greater than 0.5 mm. This simplifies the structure of the container and stabilizes the movement of the carrier elements.

Furthermore, a fluid conduit 43, a sensor 44 and an optical element 45 are provided in the container wall 41. The fluid conduit 43 comprises two lines that empty into the container 40 on sides of the container wall 41 that are located opposite each other. The fluid conduit 43 is provided in order to flow a cultivation liquid through container 40, to wash a cell to be examined (e.g. 2) into the holding area 11 and/or to remove cells from the container 40 after a test. The fluid conduit 43 has a diameter in the range of, e.g., 50 µm to a few mm.

The sensor 44 (schematically shown) contains, e.g., electrodes adapted for an impedance measuring on the cell 1. The sensor 44 is connected to a measuring instrument (not shown). The optical element 45 (schematically shown) comprises, e.g., an optical window or a connection for an optical waveguide for optical examinations (see also FIG. 2).

The conditioning device 100 according to FIG. 1 is adapted in particular for the biocompatible holding, stimulation and/or aggregation of living cells, in particular from animal or human organisms. The cell 1 is held in such a manner in the holding device 10 that it does not come in contact with biologically active substances, in particular surfaces. In order to carry out a method according to the invention, e.g., the following steps are realized. At first a cell 1 to be examined is flowed via the fluid conduit 43 (see arrow) into the holding area 11 of the holding device 10 and is trapped there in field cage 12. When the cell 1 is positioned in the field cage 12 the holding elements 13 are moved to the cell 1 in such a manner that their holding surfaces touch the cell surface. In this case the holding surfaces form a part of the holding device 10. For this the stamping surfaces have a biocompatible coating, e.g., of fibronectin or collagen.

After the formation of a molecular contact between the cell surface and the holding surfaces of the holding elements 13, which can be concluded after a few minutes, the field cage 12 can be turned off. In this situation the electrode carriers 12.3 can be withdrawn so that the cell 1 is held exclusively by the holding elements 13. This advantageously creates free space for the supplying of carrier elements to the holding area 11.

Subsequently, carrier elements (e.g., 21, 22) are pushed forward to the holding area 11. Conditioning samples comprising, e.g., biological matrix molecules such as laminin, fibronectin or collagen, a layer of immobilized, functional macromolecules that occur on a natural cell surface such as, e.g., integrins, catherins, signal receptors and the like, or a further cell 3 are located on the stamping surfaces 24 of these carrier elements 21, 22.

The touching of the cell 1 is not limited to the illustrated carrier elements 21, 22 but rather is possible with further carrier elements that are shiftably arranged in further supports in the container wall 11.

The cell 1 comes in contact with predetermined conditioning samples in a manner that can be controlled in time and spatially by a controlling of the drive device 50, in particular a timed control of the piezoelectric drives (e.g. 51). Signal chains are initiated thereby as a function of the action of the conditioning samples in cell 1 that result in a biochemical change of the cell. The biochemical change of the cell can be characterized, if necessary, after a subsequent cultivation outside of the container 40 or already directly in the holding area 11 by suitable examinations, e.g., optical or electrical measurements.

Further cells (e.g. 2) can be supplied as needed via the fluid conduit 43. As a result, cells can be combined to a cell aggregate in the holding area 11. A further possibility of adding cells to cell 1 consists in the using of one of the carrier elements (e.g. 22) on whose stamping surface a cell 3 can also be arranged.

Thus, the conditioning device 100 advantageously constitutes a system that can be universally and flexibly used for an imprinting of cells in time and space (e.g. stem cells) with a target of the differentiation and/or the tissue induction.

The illustrated embodiments of the conditioning device 100 and of the conditioning method can be modified as follows. Further measuring apparatuses such as, e.g., a pH measuring apparatus, a temperature sensor or a light sensor can be arranged in the conditioning device 100. An optical measurement can comprise in particular a scattered light measurement with which the geometric properties of the tested cell such as, e.g., the size or the nature of the surface can be tested.

The conditioning device 100 can be equipped with a regulating device in which the drive device 50 is controlled as a function of signals of the measuring apparatus.

The carrier elements and optionally the holding elements can be used for a force measuring on the cell 1. Intermolecular forces between the cell membrane and the conditioning sample can be detected with it. Furthermore, the carrier elements and optionally the holding elements can be used to bring the cell to be tested into a certain form. Furthermore, cells can be combined to cell aggregates.

Cells or cell aggregates can be loaded anisotropically with the carrier elements or optionally the holding elements with changing forces and placed or moved mechanically under stress. In this manner physiological processes such as, e.g., a bone deformation or a periodic tissue deformation can be imitated.

FIG. 2 shows a schematic sectional view of a modified variant of the embodiment according to FIG. 1 in which a plane optical window 46 and optical waveguide 47 are provided as optical elements. The cell 1 can be observed through the optical window 46 with an external measuring apparatus 60, e.g., a camera or a microscope, of which the objective 61 is illustrated. An illumination of the cell 1 takes place via the optical waveguide 47 from different sides in order to, e.g., improve the imaging with the measuring apparatus 60, make a scattered light measurement possible or to couple in excitation light for a fluorescence measuring.

FIG. 2 furthermore illustrates that the container 40 can be arranged in a vessel 70, that also contains the carrier elements (e.g. 21, 22) and the piezoelectric drives (not shown) and is completely filled with a cultivation liquid. In this case it is advantageously not necessary to seal the passage openings of the container 40, especially the support 42 (see FIG. 1).

FIG. 3 illustrates a further embodiment of the conditioning device 100 in a schematic sectional view in which the holding device 10 has a holding surface 14 on which the holding area 11 is formed. The holding device 10 is arranged in a funnel-shaped container 40. The holding surface 14 is formed between cultivation phases that comprise a lower gel layer 48 (e.g. of alginate) and an upper liquid layer 49 (e.g. of a nutrient medium). A biocompatible matrix material can be provided on the gel layer 48 for limiting the holding area 11. The position of cell 1 can be stabilized or predetermined with the biocompatible matrix material, that comprises, e.g., PTFE or another polymer. Further gels, biocompatible polymers or also test bodies with biocompatible coating can be arranged in the holding area 11 in order to define the holding area 11 for the cell 1.

The holding surface 14 can alternatively be formed by the boundary surface between two non-miscible liquid phases on which cell 1 floats. In this instance the fixation of the cell 1 in the holding area 11 is additionally stabilized by holding elements.

In a preferred application of the invention in which cellular biological processes are examined during the embryogenesis the lower gel layer 48 can comprise a biological phase such as, e.g., the yolk with surrounding membrane of a bird egg. The form of the holding surface 14 can be formed plane or curved here.

In the embodiment of the conditioning device 100 according to the invention shown in FIG. 3 the carrier elements 21, 22 are moved through the upper opening of the container 40 to the cell 1 in the holding area 11. The carrier elements 21, 22 each comprise a carrier rod 25 and a stamping surface 26 that is located on the free end of the carrier rod 25 and carries the conditioning sample 30, e.g., a further biological cell.

The container 40 is equipped with a fluid conduit 43 that forms an inflow and/or outflow to the container 40 and contains a valve. By way of example, nutrient solution and/or carrier solution can be introduced through the fluid conduit 43 in order to produce the non-miscible liquid phases.

Figure 4:
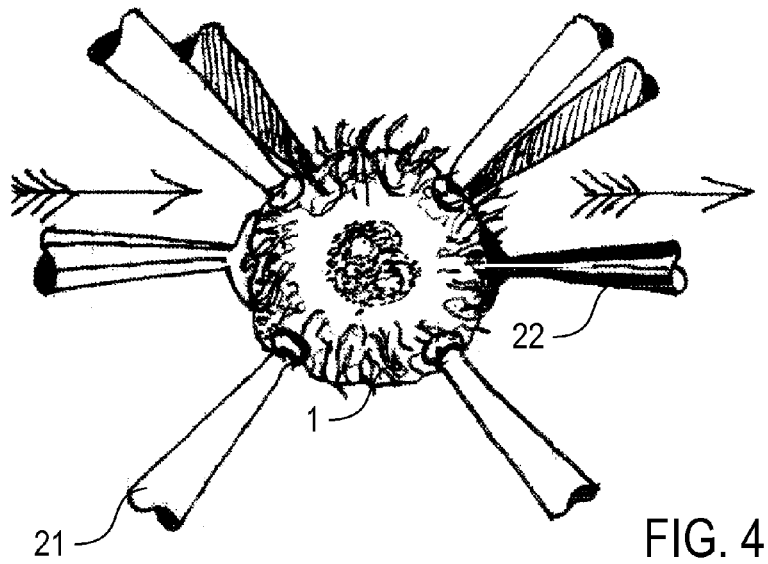
FIGS. 4 and 5 show further details of carrier elements of the conditioning device according to the invention.

FIG. 4 illustrates on an enlarged scale a cell 1 that is contacted on all sides by several carrier elements 21, 22. The cell 1 is located in a cultivation liquid that flows past the cell 1, e.g., in the direction of the arrow. The cultivation liquid contains, e.g., a nutrient solution, a solution with at least one differentiation factor and/or a solution with at least one signal factor.

At least one carrier element can comprise a hollow carrier rod 25 such as is shown by way of example for the carrier element 22. For example, hollow needles can be used as carrier elements to bring the conditioning sample in liquid form, e.g., as solution or suspension with genetic materials, cell nuclei or their components in contact with the cell 1 to be tested.

Figure 5:
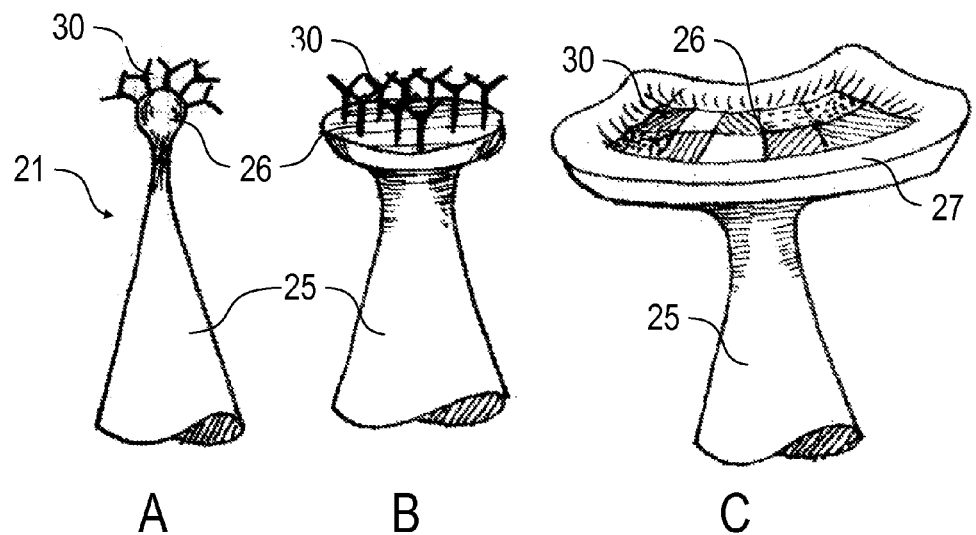

FIG. 5 illustrates by way of example variants of the carrier elements 21 used according to the invention, each of which comprising a carrier rod 25 and a stamping surface 26. According to FIG. 5A a convex, spherical stamping surface 26 is provided that carries, e.g., antibodies as conditioning sample 30. The antibodies are immobilized on the stamping surface 26 with known methods. The diameter of the stamping surfaces 26 according to FIG. 5A is selected, e.g., in the range of 5 nm to 20 µm. This advantageously minimizes the contact surface with the cell to be tested.

According to FIG. 5B a level stamping surface 26 is provided that presents a surface comparable to a conventional in vitro culture surface. The diameter of the stamping surface according to FIG. 5B is selected, e.g., in the range of 50 µm to 200 µm. Advantages of this variant of the invention result from a particularly large surface contact with the cell to be tested and the possibility of holding the cell with the stamping surface 26 and stabilizing it in its position.

FIG. 5C shows a concave stamping surface 26 by way of example, which is surrounded by an edge bead 27. Within the edge bead 27, the stamping surface 26 is structured with a pattern (e.g. chessboard pattern). The different areas in the pattern comprise, e.g., spatially separated, immobilized macromolecules comprising, e.g., predetermined signal factors or differentiation factors. The pattern and the selection of the conditioning samples can be selected as a function of the desired test task. A so-called molecular landscape is advantageously presented to the cell with the variant according to FIG. 5C that is a model for a molecular signal pattern of another cell or for a defined differentiation in the case of stem cells.

Figure 6:
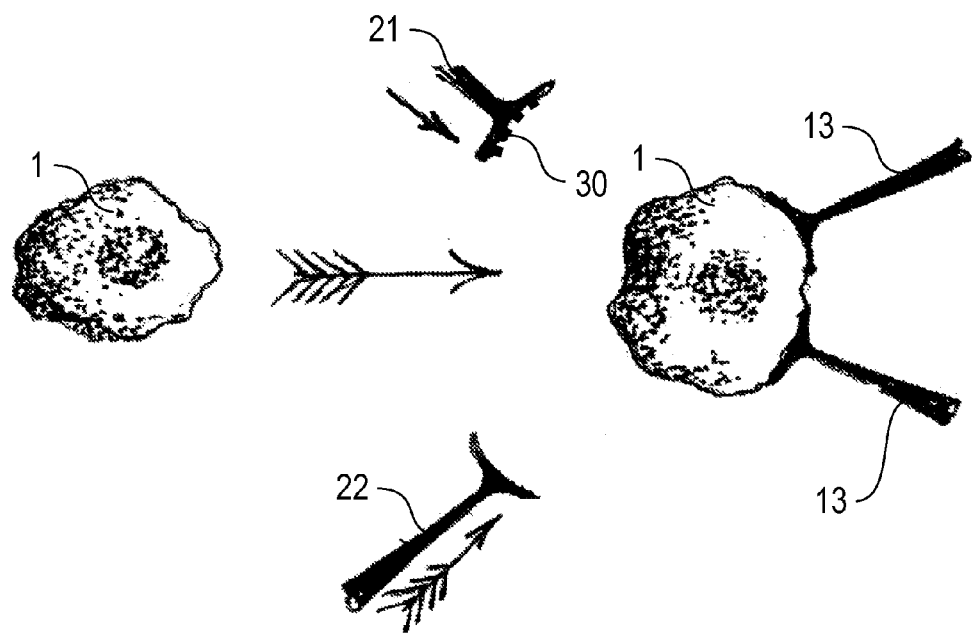
FIG. 6 shows a further illustration of an embodiment of the conditioning method according to the invention.

FIG. 6 illustrates a further variant of the conditioning method according to the invention. In a first phase the cell 1 is flowed in the direction of the arrow onto two holding elements 13. The cell 1 adheres onto the holding surfaces of the holding elements 13. Subsequently, one or several conditioning samples 30 can be brought in contact with the cell 1. This variant of the invention has the advantage that the formation of the dielectric field cage (FIG. 1) can be dispensed with. The structure of the conditioning device 100 can be correspondingly simplified.

Figure 7:
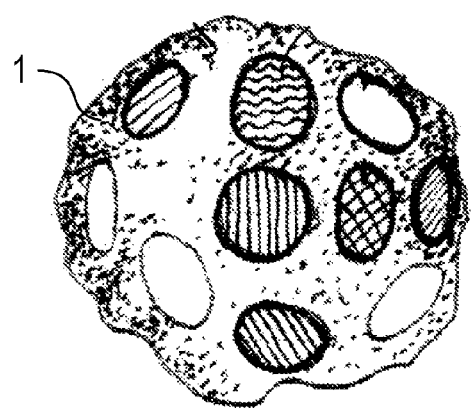
FIG. 7 shows a schematic illustration of a cell surface that was subjected to a test according to the invention.

FIG. 7 schematically shows a tested cell 1 on whose surface oval surface areas are recognizable that are or were in contact with conditioning samples, e.g., molecular patterns. The contact of the cell 1 with the different conditioning samples 30 can take place simultaneously or staggered in time at different points in time. The provision of conditioning samples with a sequence in time can be used for examinations of biological processes such as, e.g., the embryogenesis or the healing of wounds.

Figure 8:
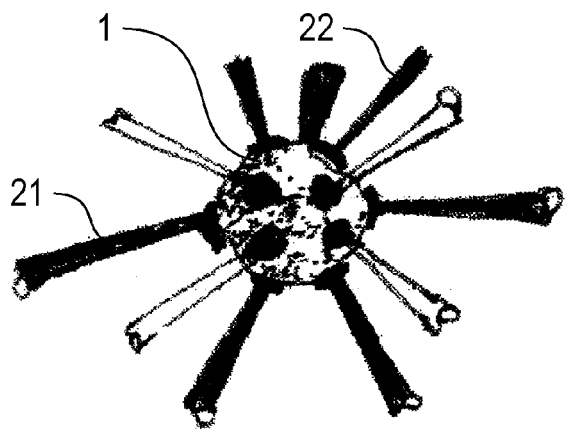
FIG. 8 shows a further application of the carrier elements according to the invention.
Figure 9:
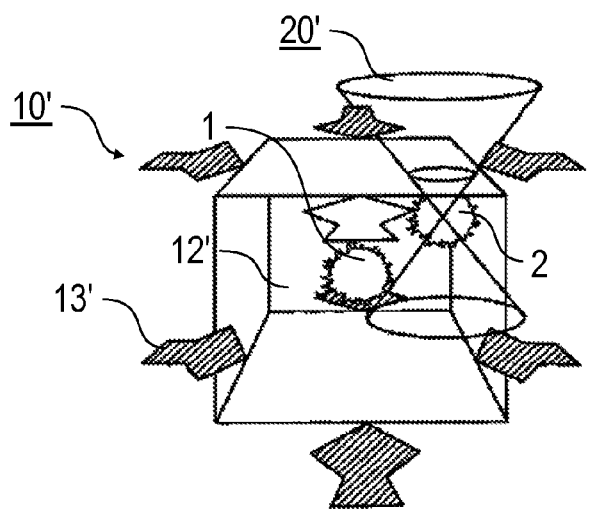
FIG. 9 shows an illustration of a conventional conditioning method (state of the art).

FIG. 8 shows a further variant of a cell 1 that is contacted on all sides by a plurality of carrier elements (e.g. 21, 22). If the lateral distances between the stamping surfaces of adjacent carrier elements are greater than or equal to 1 μm it is advantageously avoided that a cell with cell nucleus leaves the hollow space formed by the stamping surfaces of the carrier elements. Accordingly, the carrier elements, optionally in cooperation with holding elements (13, see FIGS. 1, 6), can improve the positioning of the cell 1 in the conditioning device.

A few to some 100 carrier elements can advantageously be used for a cell examination. They can be combined in such a manner, given a suitable selection of the size of the stamping surfaces, that the entire cell 1 is enclosed by the stamping surfaces of the carrier elements. The carrier elements and optional holding elements can be used to form a three-dimensionally defined space that is completely known in its surface.

The features of the invention disclosed in the previous description, the drawings and the claims can be significant individually as well as in combination for the realization of the invention in its different embodiments.

The invention claimed is:

1. A conditioning device for biological cells, comprising:
   a holding device adapted to hold at least one biological cell in a holding area, and
   a contacting device adapted to hold at least one conditioning sample and to move the at least one conditioning sample to the holding device in such a manner that the at least one conditioning sample contacts the at least one biological cell,
   wherein the contacting device has at least two mechanical carrier elements that can move from different spatial directions to the holding device.

2. The conditioning device according to claim 1, in which the holding device is adapted to hold the at least one biological cell with a force acting in a contactless manner.

3. The conditioning device according to claim 1, in which the holding device has at least one holding surface on which the at least one biological cell can be positioned.

4. The conditioning device according to claim 3, with at least one of the following features:
   the holding surface is part of at least one mechanical holding element,
   the holding surface has a boundary surface between two cultivation phases, and
   the holding surface has a biocompatible coating that is biochemically inactive for the at least one biological cell.

5. The conditioning device according to claim 1, in which the holding device is arranged in a container adapted to receive a liquid cultivation medium.

6. The conditioning device according to claim 5, in which the container has an inner volume that is greater than a four-fold volume of the at least one biological cell.

7. The conditioning device according to claim 5, in which the container comprises at least one of
   at least one support in which at least one of the mechanical carrier elements or the at least one mechanical holding element can be shifted,
   at least one fluid conduit through which a fluid connection can be established with an environment of the container,
   at least one sensor that is adapted to detect at least one physical and/or chemical quantity in the container, and
   at least one optical element adapted for an illumination and/or optical examination in the container.

8. The conditioning device according to claim 1, in which at least one of the carrier elements has a rod-shaped form.

9. The conditioning device according to claim 1, in which at least one of the carrier elements has a stamping surface adapted to receive the at least one conditioning sample.

10. The conditioning device according to claim 9, in which the stamping surface is smaller than a surface of the biological cell.

11. The conditioning device according to claim 9, in which the stamping surface has at least one of
    a concave, convex or plane form,
    a microstructuring, and
    a test coating of biologically active molecules.

12. The conditioning device according to claim 1, that further comprises a drive device, with which at least one of the carrier elements can be moved.

13. The conditioning device according to claim 12, in which the drive device contains at least one piezoelectric drive.

14. The conditioning device according to claim 12, in which the drive device is adapted to radially move the at least one carrier element to or from the holding area of the holding device.

15. The conditioning device according claim 1, in which at least ten mechanical carrier elements are provided.

16. The conditioning device according to claim 15, in which the carrier elements are adapted for a radially multi-side contacting of the at least one biological cell in the holding device.

17. A conditioning method for examining an interaction of at least one biological cell with at least one conditioning sample using a conditioning device in accordance with claim 1, comprising the steps:
    providing the at least one biological cell in the holding area of the holding device,
    providing the at least one conditioning sample on at least one of the carrier elements, and
    moving at least one of the carrier elements in such a manner that the at least one biological cell and the at least one conditioning sample mutually contact each other.

18. The method according to claim 17, further comprising the step of examining the at least one biological cell.

19. The method according to claim 17, in which several conditioning samples simultaneously contact the at least one biological cell.

20. The method according to claim 17, in which several conditioning samples contact the at least one biological cell staggered in time.

21. The method according to claim 17, in which the conditioning sample is selected from the group consisting of biologically active macromolecules, signal molecules, biological cells, cell components and microstructured surfaces.

22. The method according to claim 17, in which the providing of the at least one biological cell takes place with an optical tweezer, a dielectric cage or an ultrasonic trap.

23. The method according to claim 17, in which the at least one carrier element is moved with a speed selected in a range of 5 μm/h to 10 mm/h.

24. The method according to claim 17, in which several cells are grouped in the holding area.

25. The method according to claim 17, further comprising at least one of the following steps:
    providing a conditioning sample as component of a cultivation liquid that surrounds the at least one biological cell,
    forming of a hollow space surrounding the at least one biological cell, which hollow space is enclosed by at least one of stamping surfaces of carrier elements and holding surfaces of holding elements, measuring of interactive forces between the at least one biological cell and the at least one conditioning sample,
mechanically deforming the at least one biological cell,
liquid treatment of the at least one biological cell,
cultivating of the at least one biological cell,
encapsulating of the at least one biological cell, and
transferring of the at least one biological cell into a frozen state.

* * * * *